US005958426A

United States Patent [19]
Moreau et al.

[11] Patent Number: 5,958,426
[45] Date of Patent: Sep. 28, 1999

[54] SPHINGOLIPIDS AND A PROCESS THERETO

[75] Inventors: Robert Arthur Moreau, Quakertown; David Hamilton Young, Ambler; Ronald Ross, Jr., Jamison, all of Pa.

[73] Assignees: The United States of America as represented by the Secretary of Agriculture, Washington, D.C.; Rohm and Haas Company,, Phila., Pa.

[21] Appl. No.: 08/824,646

[22] Filed: Mar. 24, 1997

Related U.S. Application Data

[60] Provisional application No. 60/014,326, Mar. 29, 1996.

[51] Int. Cl.$^6$ ..................................................... A61K 45/00
[52] U.S. Cl. ........................................................... 424/283.1
[58] Field of Search ......................... 424/283.1; 514/119; 564/15

[56] References Cited

U.S. PATENT DOCUMENTS 4,937,232  6/1990  Bell et al. .................................. 514/26

OTHER PUBLICATIONS

Pivot et al., "Isolation, Characterization and Biological Activity of Inositol Sphingolipids. . .," Lipids 29(1994) pp. 21–25.

Jin et al., "Ophidiacerebrosides: Cytotoxic Glyco–Sphingolipids. . ." Jorg Chem 59:144–147 (1994).

Lhomme et al., "Structural Investigations and Biological. . ." Eur J Biochem 191:203–209 (1990).

Itasaka et al., "Analysis of Phospho–and Phosphono–Sphingolipids. . ." J Biochem 95:1671–75, (1984).

Kaneshiro et al., "Characterizations of six ethanolamine. . .," J Lipid Res 25:369–377 (1984).

Stein et al., "Ceramid–1–Phosphoethanolamine. . .," Z. Naturforsch 43b:1063–1067 (1988).

*Primary Examiner*—Donna C. Wortman
*Assistant Examiner*—Brenda G. Brumback
*Attorney, Agent, or Firm*—Clark R. Carpenter

[57] ABSTRACT

A process for novel sphingolipids and other secondary sphingosine-based compounds is provided which comprises the culturing of an appropriate fungus, harvesting mycelium from the fungus and isolating the sphingolipid from the mycelium. The sphingosine-based materials inhibit protein kinase C, provide an anti-inflammatory effect or provide an anti-tumor effect; furthermore, these sphingosine-based materials provide protection for plants against pathogenic microorganisms.

17 Claims, No Drawings

SPHINGOLIPIDS AND A PROCESS THERETO

This is a nonprovisional application of prior pending provisional application Ser. No. 60/014,326, filed Mar. 29, 1996

This invention relates to a process for the preparation of sphingolipids. Furthermore, some of the sphingolipids of this invention possess a highly unusual branched, polyunsaturated sphingosine moiety which has been reported previously {Kenneth L. Rinehart et al., "Ophidiacerebrosides: Cytotoxic Glycosphingolipids Containing a Novel Sphingosine from a Sea Star", *J. Org. Chem.* 1994 (59), pp. 144–147} to be present in cytotoxic cerebrosides from starfish. Sphingosines and sphingolipids exert many effects on mammalian cells {reviewed by S. Spiegel and S. Milstein, *J. Membrane Biol.* 146, 225 (1995)} and are useful as inhibitors of protein kinase C (U.S. Pat. No. 4,937,232) whereby such sphingosines and sphingolipids may be of therapeutic value in a number of disease states such as cancer, rheumatoid arthritis, diabetic complication, central nervous system disorders, etc. Furthermore, inositol sphingophospholipids and ceramide aminoethylphosphonate represent two types of sphingolipids which have been described in fungi of the class Oomycetes and which demonstrate biological activity. Inositol sphingophospholipids from *Phytophthora capsici* have a protective effect on pepper plants against pathogenesis by *P. capsici* (*European Journal of Biochemistry*, 1

Formula (IA) was determined by mass spectrometry and nmr using methods well known to those of ordinary skill in the art. Heterogeneity was found in the fatty acid component of the sphingolipid.

Sphingolipid of Formula IA:

[Chemical structure of Sphingolipid Formula IA]

EXAMPLE 2
Isolation and characterization of sphingolipids from *Phytophthora infestans*:

Phytophthorn infestans (A1 strain) was maintained on pea juice medium or rye A agar {C. E. Caten and J. L. Jinks, (1968), *Canadian Journal of Botany* 46, page 329}. Pea juice medium was prepared by autoclaving 283 g of frozen peas in one liter of distilled water, stirring the autoclaved peas vigorously and straining through cheesecloth. Agar, 20 g, was added to the filtrate which was then autoclaved again before pouring culture plates. Petri dishes, 9 cm in diameter, containing 20 mL of liquid asparagine-sucrose medium were inoculated with a mycelial plug, 7 mm in diameter, taken from the growing edge of a culture grown on pea juice medium or rye A agar. The dishes were incubated for 20 days at 25° C. with shaking on a gyrotary shaker at 60 rpm. Mycelium was then harvested by filtration on glass fiber filters, washed with water and freeze-dried.

The major sphingolipid from *Phytophthora infestans* was extracted and isolated as described in Example 4 and is shown as Formula (IB). Heterogeneity was found in the fatty acid component of the sphingolipid. The structure of the sphingolipid of Formula (IB) was determined by mass spectrometry and nmr using methods well known to those of ordinary skill in the art.

Sphingolipid of Formula IB:

[Chemical structure of Sphingolipid Formula IB]

EXAMPLE 3
Isolation and characterization of sphingolipids from *Phytophthora capsici*

*Phytophthora capsici* (ATCC 15399) was maintained on V8-juice agar, pH 7.0, containing 200 mL V-8 juice, 4 g CaCO$_3$, and 20 g agar per liter. Petri dishes, 9 cm in diameter, containing 20 mL of liquid asparagine-sucrose medium were inoculated with a mycelial plug, 7 mm in diameter, taken from the growing edge of a culture grown on V8-juice agar. The dishes were incubated for 96 h at 25° C. with shaking on a gyrotary shaker at 60 rpm. Mycelium was then harvested by filtration on glass fiber filters, washed with water and freeze-dried.

Two major sphingolipids identical to Formulas (IA) and (IB) above were isolated from *Phytophthora capsici* as described in Example 4.

EXAMPLE 4
Lipid Extraction and Chromatography Isolation Procedure

Sphingolipids were extracted from lyophilized fungal cells (200 mg) prepared as in Examples 1, 2 and 3 using chloroform (8 mL), methanol (16 mL), water (4.6 mL) by homogenizing for 30 sec with a Polytron Homogenizer (Brinkman) in a 20×200 mm screw top tube fitted with a Teflon cap. After homogenization, additional chloroform (8 mL) and water (8 mL) were added. The extracts were mixed by inverting them 30 times and the extract was centrifuged at 70×g for 10 min, twice, to separate the phases. The lower chloroform phase was removed, evaporated under a stream of nitrogen gas, redissolved in 1 mL chloroform/methanol (85/15, v/v), and filtered through glass wool.

The entire lipid extract (6–20 mg in 1 mL) was separated by semi-preparative HPLC. The column (10×250 mm) contained LiChrosorb Silica, 10 micron, 60 Angstrom, and the mobile phase gradient was A) hexane, B) isopropanol, and C) 0.04% triethylamine in water at a flow rate of 5 mL/min. The linear gradient timetable was: 0 min, 100/0/0; 8 min, 100/0/0; 13 min, 95/5/0; 18 min, 85/15/0; 23 min, 40/60/0; 61 min, 40/51/9; 76 min, 40/51/9; 81 min, 40/60/0; 86 min, 100/0/0; 100 min, 100/0/0; for % A/% B./% C, respectively. The quaternary gradient HPLC system was a Hewlett Packard Model 1050. The injector was a Rheodine model 7125, fitted with a 1.0 mL fixed loop. The effluent from the column was split with a Valco "T", with 97% of the sample being collected in a test tube and 3% of the sample being detected by an Varex Mark II Evaporative Light-Scattering Detector operated at 40° C., with nitrogen as a nebulizing gas at 20 psi. Under these conditions, phosphatidylethanolamine eluted at a retention time of 48 min, ceramide-PE (the sphingolipid of Formula IB) from *Phytophthora infestans* was collected at about 49 min, and ceramide-PE (the sphingolipid of Formula IA) from *Pythium ultimum* was collected at about 50 min. The lipids from *Phytophthora capsici* contained two ceramide-PE peaks, one (Formula IB) was collected at 49 min and and the second (Formula IA) at 50 min.

A second embodiment of the present invention is concerned with a process for the preparation of sphingosines, sphingosinephosphorylethanolamines and ceramides from the novel sphingolipids produced by the process as described in the previous embodiment. These sphingosines, sphingosinephosphorylethanolamines and ceramides are extremely useful as compounds used in the preparation of subsequent other novel as well as known and useful sphingolipids.

Thus, this embodiment provides a process for preparing sphingosines, sphingosinephosphorylethanolamines and ceramides comprising the steps of (i) culturing an appropriate fungus,
(ii) harvesting mycelium from said fungus,
(iii) isolating from said mycelium the sphingolipid of the formula

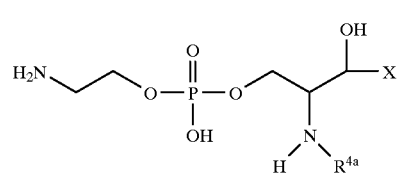

(I)

wherein $R^{4a}$ is $C(O)R^{8a}$;

$R^{8a}$ is $(C_{13}-C_{23})$alkyl, $(C_{13}-C_{23})$alkenyl or poly$(C_{13}-C_{23})$alkenyl, all of which may be a straight or a branched chain;

X is a branched or straight chain alkyl, alkenyl or polyalkenyl; and (iv) modifying said sphingolipid by selective hydrolysis to form (a) a sphingosine of formula (II)

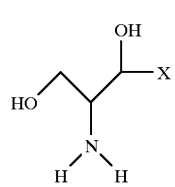

(II)

wherein

X is a branched or straight chain alkyl, alkenyl or polyalkenyl;

(b) a sphingosinephosphorylethanolamine of formula (III)

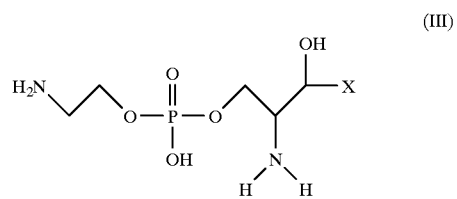

(III)

wherein

X is a branched or straight chain alkyl, alkenyl or polyalkenyl; or (c) a ceramide of formula (IV)

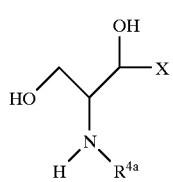

(IV)

wherein $R^{4a}$ is $C(O)R^{8a}$;

$R^{8a}$ is $(C_{13}-C_{23})$alkyl, $(C_{13}-C_{23})$alkenyl or poly$(C_{13}-C_{23})$alkenyl, all of which may be a straight or a branched chain;

X is a branched or straight chain alkyl, alkenyl or polyalkenyl; and the enantiomorphs and structural isomers thereof.

In a preferred embodiment, the process for preparing a sphingosine of formula (II), a sphingosinephosphorylethanolamine of formula (III) or a ceramide of formula (IV) wherein X is $(C_{10}-C_{20})$alkyl, $(C_{10}-C_{20})$alkenyl or poly$(C_{10}-C_{20})$alkenyl, all of which may be a straight or a branched chain; comprises culturing an appropriate Oomycete fungus in step (i).

In a more preferred embodiment, the process produces a sphingosine of formula (II), a sphingosinephosphorylethanolamine of formula (III) or a ceramide of formula (IV) wherein X is $(C_{10}-C_{20})$alkenyl or poly$(C_{10}-C_{20})$alkenyl, all of which may be a straight or a branched chain.

In an even more preferred embodiment, the process produces a sphingosine of formula (II), a sphingosinephosphorylethanolamine of formula (III) or a ceramide of formula (IV) wherein X is a branched chain $(C_{14}-C_{18})$alkatrienyl or a straight chain $(C_{11}-C_{15})$alkenyl and $R^{8a}$ is a straight chain $(C_{13}-C_{23})$alkyl, $(C_{13}-C_{23})$alkenyl or poly$(C_{13}-C_{23})$alkenyl.

The following compounds can be made and are meant to illustrate, but not limit, the scope of this embodiment of the invention:

Sphingosine of Formula IIA
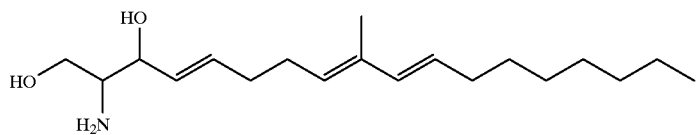
Sphingosine of Formula IIB
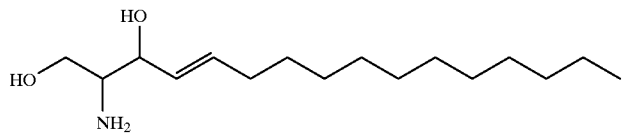
Sphingosinephosphorylethanolamine of Formula IIIA
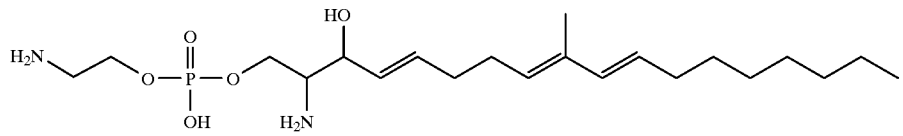
Sphingosinephosphorylethanolamine of Formula IIIB
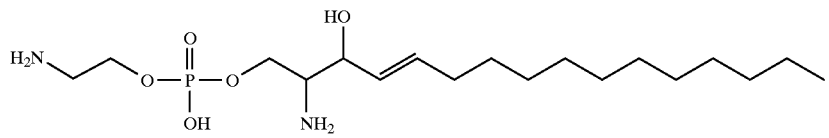
Ceramide of Formula IVA
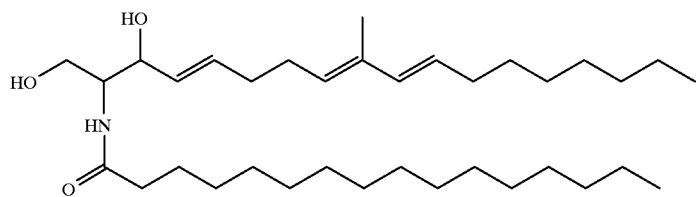
Ceramide of Formula IVB
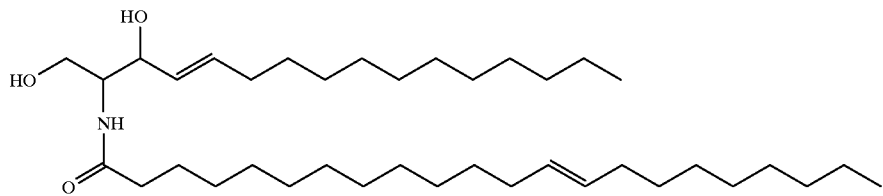

The above sphingosines IIA and IIB, sphingosinephosphorylethanolamines IIIA and IIIB, and ceramides IVA and IVB can be made from sphingolipids IA and IB using the procedures described in Examples 5–10 which are used to illustrate, but not limit, the scope of the invention.

EXAMPLE 5
Conversion of IA to IIA

Sphingolipid IA is converted to spingosine IIA by methanolysis in methanolic HCl (1N) according to the method of Gaver, R. C., and Sweeley, C. C. (1965) *J. Am. Oil Chem. Soc.* 42:294–298. After methanolysis the methanol and HCl are removed by evaporation in a stream of nitrogen at room temperature. Spingosine IIA is purified from the starting material and any other contaminating materials by redissolving the hydrolysate in 1 mL chloroform/methanol, 85/15, v/v, and injecting it in the semiprep HPLC system described for the initial purification of sphingolipid IA. In this HPLC system Spingosine IIA elutes at a retention time of about 34 min.

EXAMPLE 6
Conversion of IB to IIB

Sphingolipid IB is converted to sphingosine IIB by hydrolysis in methanolic HCl (1N) according to the method of Gaver, R. C., and Sweeley, C. C. (1965) *J. Am. Oil Chem. Soc.* 42:294–298. After methanolysis the methanol and HCl are removed by evaporation in a stream of nitrogen at room temperature. Sphingosine IIB is purified from the starting material and any other contaminating materials by redissolving the hydrolysate in 1 mL chloroform/methanol, 85/15, v/v, and injecting it in the semi-prep HPLC system described for the initial purification of sphingolipid IA. In this HPLC system sphingosine IIB elutes at a retention time of about 36 min.

EXAMPLE 7
Conversion of IA to IIIA

Sphingolipid IA is converted to sphingosinephosphorylethanolamine IIIA either by a) alkaline hydrolysis according to the method of Neuenhofer, S., Schwarzmain, G., Egge, H., Sandhoff, K. (1985) *Biochemistry* 24:525–529 or b) enzymatic hydrolysis with sphingolipid ceramide N-deacylase according to the method of Ito, M., Kurita, T., and Kita, K. (1995) *J. Biol. Chem.* 270:24370–374. Sphingosinephosphorylethanolamine IIIA is purified from the starting material and any other contaminating materials by redissolving the hydrolysate in 1 mL chloroform/methanol, 85/15, v/v, and injecting it in the semiprep HPLC system described for the initial purification of sphingolipid IA. In this HPLC system sphingosinephosphorylethanolamine IIA elutes at a retention time of about 54 min.

EXAMPLE 8
Conversion of IB to IIIB

Sphingolipid IB is converted to sphingosinephosphorylethanolamine IIIB either by a) alkaline hydrolysis according to the method of Neuenhofer, S., Schwarzmann, G., Egge, H., Sandhoff, K. (1985) *Biochemisty* 24:525–529 or b) enzymatic hydrolysis with sphingolipid ceramide N-deacylase according to the method of Ito, M., Kurita, T., and Kita, K. (1995) *J. Biol. Chem.* 270:24370–374. Sphingosinephosphorylethanolamine IIIB is purified from the starting material and any other contaminating materials by redissolving the hydrolyate in 1 ml chloroform/methanol, 85/15, v/v, and injecting it in the semi-prep HPLC system described for the initial purification of sphingolipid IA. In this HPLC system sphingosinephosphorylethanolamine IIIB elutes at a retention time of about 55 min.

EXAMPLE 9
Conversion of IA to IVA

Sphingolipid IA is converted to ceramide IVA by treatment with phospholipase C according to the method of Morrison, W. R. (1969) *Biochim. Biophys. Acta.* 176:537–546. Ceramide IVA is purified from the starting material and any other contaminating materials by redissolving the hydrolysate in 1 mL chloroform/methanol, 85/15, v/v, and injecting it in the semi-prep HPLC system described for the initial purification of sphingolipid IA. In this HPLC system ceramide IVA elutes at a retention time of about 22 min.

EXAMPLE 10
Conversion of IB to IVB

Sphingolipid IB is converted to ceramide IVB enzymatically by treatment with phospholipase C according to the method of Morrison, W. R. (1969) *Biochim. Biophys. Acta.* 176:537–546. Ceramide IVB is purified from the starting material and any other contaminating materials by redissolving the hydrolysate in 1 mL chloroform/methanol, 85/15, v/v, and injecting it in the semi-prep HPLC system described for the initial purification of sphingolipid IA. In this HPLC system ceramide WVB elutes at a retention time of about 23 min.

In a third embodiment of this invention, there is provided a process for preparing secondary or daughter sphingolipids of formula V

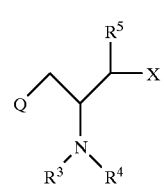

(V)

wherein
  $R^5$ is a hydrogen atom, hydroxyl, mercapto, amino, monosubstituted amino, disubstituted amino or a disubstituted amino in which the two substituents together with the nitrogen atom to which they are attached form a nitrogen atom containing heterocyclic ring of 3 to 7 ring members, $OC(O)R^6$ or $OR^6$, or together with the carbon to which it is attached forms a keto group;
  $R^6$ is $(C_1-C_6)$alkyl, $(C_2-C_6)$alkenyl, $(C_2-C_6)$alkynyl, aralkyl or heterocyclylalkyl;
  Q is any organic group, a phosphate or substituted phosphate, or a phosphonate or substituted phosphonate, and is not necessarily further limited;
  $R^3$ and $R^4$ are independently a hydrogen atom, lower alkyl, $C(O)R^8$, $C(O)OR^8$ or together with the nitrogen atom to which they are attached form a nitro group or a nitrogen atom containing heterocyclic ring of 3–7 ring members;
  $R^8$ is $(C_1-C_{23})$alkyl, $(C_2-C_{23})$alkenyl, poly$(C_4-C_{23})$ alkenyl, $(C_2-C_{23})$alkynyl, aralkyl or heterocyclylalkyl which is cyclic, branched or straight chain, and which may be substituted by one or more conventional pharmaceutically acceptable substituents such as halo, nitro, hydroxyl and the like, and
  the enantiomorphs and structural isomers thereof; comprising steps (i), (ii), (iii) and (iv) of the second embodiment and
  (v) reacting a sphingosine of formula (II), a sphingosinephosphorylethanolamine of formula (III) or a ceramide of formula (IV) with one or more suitable organic reactants to form the desired daughter sphingolipid of formula (V).

In a preferred embodiment, the process produces a daughter sphingolipid of formula (V) wherein $R^5$ is a hydrogen atom, hydroxyl, mercapto, amino, mono-substituted amino, substituted amino, OC(O)$R^6$ or O$R^6$, or together with the carbon to which it is attached forms a keto group;

$R^6$ is ($C_1$–$C_6$)alkyl, ($C_2$–$C_6$)alkenyl, ($C_2$–$C_6$)alkynyl, aralkyl or heterocyclylalkyl which is cyclic, branched or straight chain, and which may be substituted by one or more conventional pharmaceutically acceptable substituents such as halo, nitro, hydroxyl and the like;

Q is a hydrogen atom, hydroxy, mercapto, N$R^1R^2$, formyl, alkanoyl, OC(O)$R^6$, O$R^6$, a phosphate or substituted phosphate, a phosphonate or substituted phosphonate, a nucleotide, a nucleoside, a polynucleotide, a polynucleoside, an amino acid, a peptide, a saccharide or a polysaccharide;

$R^1$ and $R^2$ are independently a hydrogen atom, lower alkyl, C(O)$R^7$, C(O)O$R^7$ or together with the nitrogen atom to which they are attached form a nitro group or a nitrogen atom containing heterocyclic ring of 3–7 ring members;

$R^7$ is alkyl, alkenyl, alkynyl, aralkyl or heterocyclylalkyl which is cyclic, branched or straight chain, and which may be substituted by one or more conventional pharmaceutically acceptable substituents such as halo, nitro, hydroxyl and the like;

$R^3$ and $R^4$ are independently a hydrogen atom, lower alkyl, C(O)$R^8$, C(O)O$R^8$ or together with the nitrogen atom to which they are attached form a nitro group or a nitrogen atom containing heterocyclic ring of 3–7 ring members;

$R^8$ is ($C_1$–$C_{23}$)alkyl, ($C_2$–$C_{23}$)alkenyl, poly($C_4$–$C_{23}$) alkenyl, ($C_2$–$C_{23}$)alkynyl, aralkyl or heterocyclylalkyl which is cyclic, branched or straight chain, and which may be substituted by one or more conventional pharmaceutically acceptable substituents such as halo, nitro, hydroxyl and the like; and the enantiomorphs and structural isomers thereof.

In a more preferred embodiment, the process produces a daughter sphingolipid of formula (V) wherein Q is selected from the group consisting of hydroxyl, glycyl, arginyl, lysyl, galactosyl, sulfogalactosyl, glucosyl, inositol, lactosyl, trihexosyl, phosphorylcholine, phosphorylethanolamine, GalNAc-Gal-Glc, Gal-Gal-Glc, Sia-Gal-Glc,

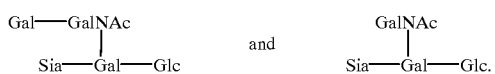

In an even more preferred embodiment, the process produces a daughter sphingolipid of formula (V) wherein Q is glucosyl, $R^8$ is CH(OH)—(CH$_2$)$_n$CH$_3$ and n is 11–21.

By GalNAc is meant N-acetyl galactosamine; by Glc is meant glucose. by Gal is meant galactose, and by Sia is meant sialic acid. By trihexosyl is meant polysaccharides composed of three hexoses such as galactose, glucose, mannose etc. Both D and L isomers are contemplated.

Examples of compounds which can be made by the process of this last embodiment include, but are not limited to the following:

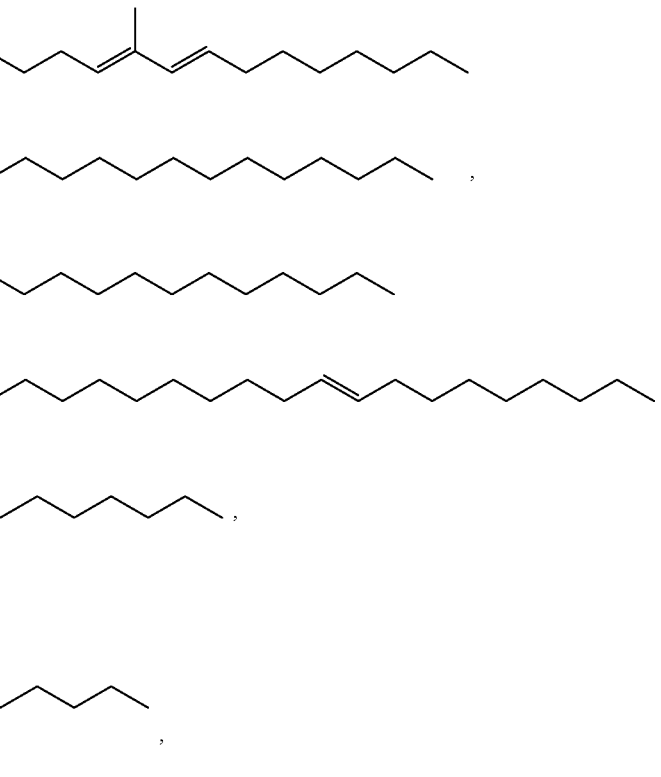

-continued

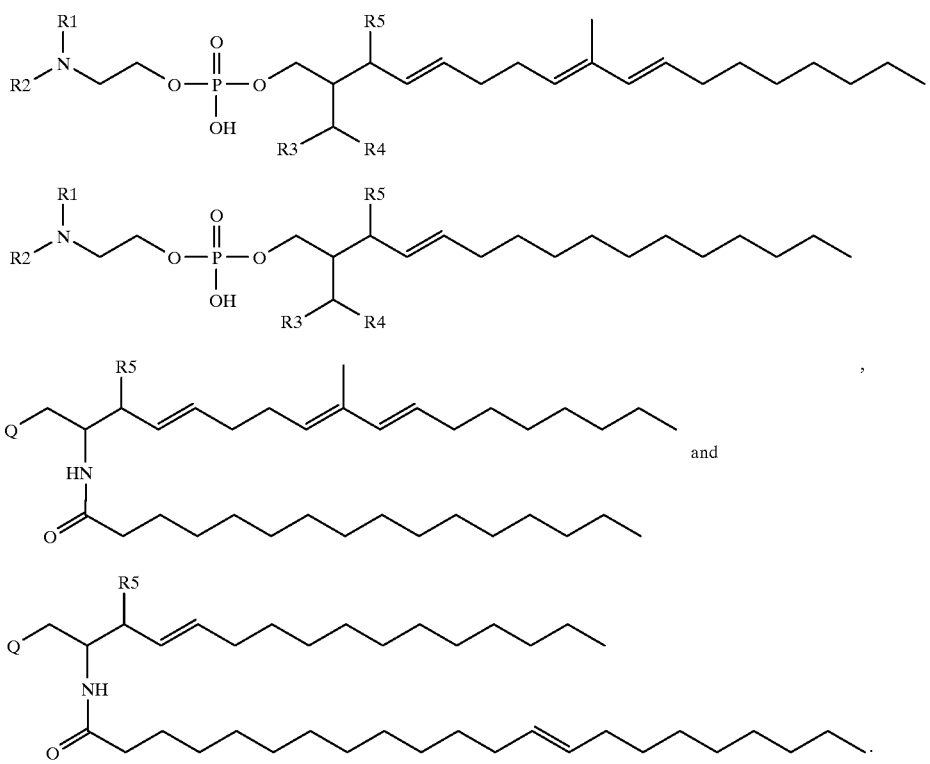

In a fourth embodiment of this invention a method is provided which comprises the contact of a mammalian cell with a therapeutically effective amount of a compound of formula (I), (II), (III), (IV) or (V) in the presence of a pharmaceutically acceptable carrier in order to inhibit protein kinase C, to provide an anti-inflammatory effect or to provide an anti-tumor effect.

In a fifth embodiment of this invention a method is provided which comprises the treatment of a plant with an agronomically effective amount of a compound of formula (I), (IH), (III), (IV) or (V) in the presence of an agronomically acceptable carrier in order to provide a protective effect against plant pathogenic microorganisms.

We claim:

1. A process for preparing a sphingolipid mixture of the formula

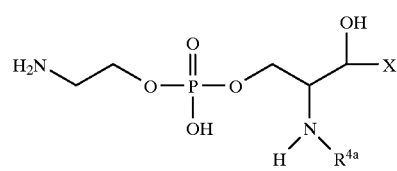

(I)

wherein
$R^{4a}$ is $C(O)R^{8a}$;
$R^{8a}$ is $(C_{13}-C_{23})$alkyl, $(C_{13}-C_{23})$alkenyl or poly$(C_{13}-C_{23})$alkenyl, all of which may be a straight or a branched chain;
X is a branched or straight chain alkyl, alkenyl or polyalkenyl; and the enantiomorphs and structural isomers thereof; comprising the steps of
(i) culturing an appropriate Oomycete fungus,
(ii) harvesting mycelium from said fungus, and
(iii) isolating the sphingolipid from said mycelium.

2. The process of claim 1 for preparing a sphingolipid mixture of formula (I), wherein
X is $(C_{10}-C_{20})$alkyl, $(C_{10}-C_{20})$alkenyl or poly$(C_{10}-C_{20})$alkenyl, all of which may be a straight or a branched chain;
comprising culturing an appropriate Oomycete fungus in step (i).

3. The process of claim 2 for a sphingolipid mixture of formula (I) wherein
X is $(C_{10}-C_{20})$alkenyl or poly$(C_{10}-C_{20})$alkenyl, all of which may be a straight or a branched chain.

4. The process of claim 3 for a sphingolipid mixture of formula (I) wherein
X is a branched chain $(C_{14}-C_{18})$alkatrienyl or a straight chain $(C_{11}-C_{15})$alkenyl and
$R^{8a}$ is a straight chain $(C_{13}-C_{23})$alkyl, $(C_{13}-C_{23})$alkenyl or poly$(C_{13}-C_{23})$alkenyl.

5. A compound of formula (I) or a mixture thereof

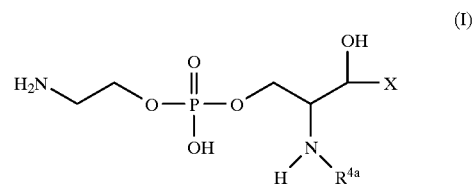

(I)

wherein
$R^{4a}$ is $C(O)R^{8a}$;
$R^{8a}$ is $C_{13}$ alkyl, $C_{15}$ alkyl, $C_{19}$ alkyl, $C_{21}$ alkyl, $C_{17}$ alkenyl, $C_{19}$ alkenyl, $C_{21}$ alkenyl or poly$(C_{13}-C_{23})$ alkenyl, all of which may be a straight or a branched chain;

X is alkyl, $C_{11}$ alkenyl, $C_{13}$ alkenyl, $C_{15}$ alkenyl, $C_{17}$ alkenyl, $C_{19}$ alkenyl, $C_{21}$ alkenyl or polyalkenyl, all of which may be a straight or a branched chain;

provided that when $R^{8a}$ is $C_{15}$alkyl, X is not $C_{15}$ alkenyl; and the enantiomorphs and structural isomers thereof.

6. The compound of claim 5 or a mixture thereof wherein X is $(C_{10}-C_{20})$alkyl, $C_{11}$ alkenyl, $C_{13}$ alkenyl, $C_{15}$ alkenyl, $C_{17}$ alkenyl, $C_{19}$ alkenyl, or poly$(C_{10}-C_{20})$alkenyl, all of which may be a straight or a branched chain.

7. The compound of claim 6 or a mixture thereof wherein

X is $C_{11}$ alkenyl, $C_{13}$ alkenyl, $C_{15}$ alkenyl, $C_{17}$ alkenyl, $C_{19}$ alkenyl, or poly$(C_{10}-C_{20})$alkenyl, all of which may be a straight or a branched chain.

8. The compound of claim 7 or a mixture thereof wherein

X is a branched chain $(C_{14}-C_{18})$alkatrienyl or a straight chain $C_{11}$ alkyenl, $C_{13}$ alkenyl, or $C_{15}$ alkenyl, and $R^{8a}$ is a straight chain $C_{13}$ alkyl, $C_{15}$ alkyl, $C_{19}$ alkyl, $C_{21}$ alkyl, $C_{17}$ alkenyl, $C_{19}$ alkenyl, $C_{21}$ alkenyl or poly$(C_{13}-C_{23})$alkenyl.

9. A process for preparing sphingosines, sphingosinephosphorylethanolamines and ceramides comprising the steps of (i) culturing an appropriate Oomycete fungus, (ii) harvesting mycelium from said fungus, (iii) isolating from said mycelium a sphingolipid mixture of the formula

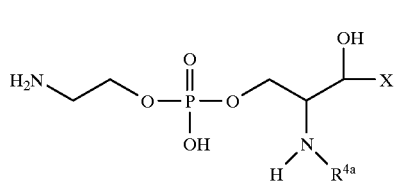
(I)

wherein $R^{4a}$ is $C(O)R^{8a}$;

$R^{8a}$ is $(C_{13}-C_{23})$alkyl, $(C_{13}-C_{23})$alkenyl or poly$(C_{13}-C_{23})$alkenyl, all of which may be a straight or a branched chain;

X is a branched or straight chain alkyl, alkenyl or polyalkenyl; and (iv) modifying said sphingolipid mixture by selective hydrolysis to form (a) a sphingosine of formula (II)

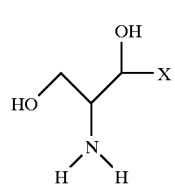
(II)

wherein

X is a branched or straight chain alkyl, alkenyl or polyalkenyl;

(b) a sphingosinephosphorylethanolamine of formula (III)

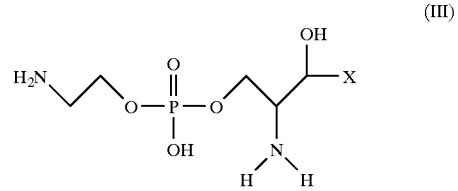
(III)

wherein

X is a branched or straight chain alkyl, alkenyl or polyalkenyl; or (c) a ceramide mixture of formula (IV)

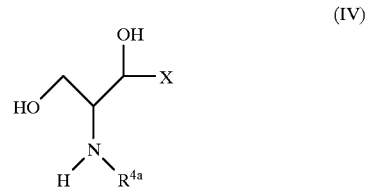
(IV)

wherein $R^{4a}$ is $C(O)R^{8a}$;

$R^{8a}$ is $(C_{13}-C_{23})$alkyl, $(C_{13}-C_{23})$alkenyl or poly$(C_{13}-C_{23})$alkenyl, all of which may be a straight or a branched chain;

X is a branched or straight chain alkyl, alkenyl or polyalkenyl; and ps the enantiomorphs and structural isomers thereof.

10. The process of claim 9 for preparing a sphingosine of formula (II) a sphingosinephosphorylethanolamine of formula (III) or a ceramide mixture of formula (IV) wherein X is $(C_{10}-C_{20})$alkyl, $(C_{10}-C_{20})$alkenyl or poly$(C_{10}-C_{20})$alkenyl, all of which may be a straight or a branched chain.

11. The process of claim 10 for preparing a sphingosine of formula (II), a sphingosinephosphorylethanolamine of formula (III) or a ceramide mixture of formula (IV) wherein X is $(C_{10}-C_{20})$alkenyl or poly$(C_{10}-C_{20})$alkenyl, all of which may be a straight or a branched chain.

12. The process of claim 11 for preparing a sphingosine of formula (II), a sphingosinephosphorylethanolamine of formula (III) or a ceramide mixture of formula (IV) wherein X is a branched chain $(C_{14}-C_{18})$alkatrienyl or a straight chain $(C_{11}-C_{15})$alkenyl and $R^{8a}$ is a straight chain $(C_{13}-C_{23})$alkyl, $(C_{13}-C_{23})$alkenyl or poly$(C_{13}-C_{23})$alkenyl.

13. A process for preparing secondary or daughter sphingolipids of formula V

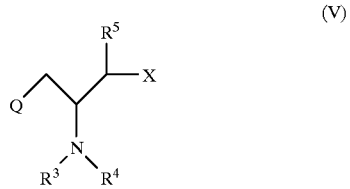
(V)

wherein $R^5$ is a hydrogen atom, hydroxyl, mercapto, amino, monosubstituted amino, disubstituted amino or a disubstituted amino in which the two substituents together with the nitrogen atom to which they are attached form a nitrogen atom containing heterocyclic ring of 3 to 7 ring members, $OC(O)R^6$ or $OR^6$, or together with the carbon to which it is attached forms a keto group;

$R^6$ is $(C_1-C_6)$alkyl, $(C_2-C_6)$alkenyl, $(C_2-C_6)$alkynyl, aralkyl or heterocyclylalkyl;

Q is any organic group, a phosphate or substituted phosphate, or a phosphonate or substituted phosphonate, and is not necessarily further limited;

$R^3$ and $R^4$ are independently a hydrogen atom, lower alkyl, $C(O)R^8$, $C(O)OR^8$ or together with the nitrogen atom to which they are attached form a nitro group or a nitrogen atom containing heterocyclic ring of 3–7 ring members;

$R^8$ is $(C_1-C_{23})$alkyl, $(C_2-C_{23})$alkenyl, poly$(C_4-C_{23})$alkenyl, $(C_2-C_{23})$alkynyl, aralkyl or heterocyclylalkyl which is cyclic, branched or straight chain, and which may be substituted by one or more conventional pharmaceutically acceptable substituents such as halo, nitro, hydroxyl and the like, and the enantiomorphs and structural isomers thereof; comprising the steps of
(i) culturing an appropriate Oomycete fungus,
(ii) harvesting mycelium from said fungus,
(iii) isolating from said mycelium a sphingolipid mixture of the formula

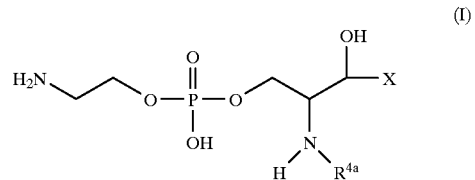

(I)

wherein $R^{4a}$ is $C(O)R^{8a}$;

$R^{8a}$ is $(C_{13}-C_{23})$alkyl, $(C_{13}-C_{23})$alkenyl or poly $(C_{13}-C_{23})$alkenyl, all of which may be a straight or a branched chain;

X is a branched or straight chain alkyl, alkenyl or polyalkenyl;

(iv) modifying said sphingolipid mixture by selective hydrolysis to form
(a) a sphingosine of formula (II)

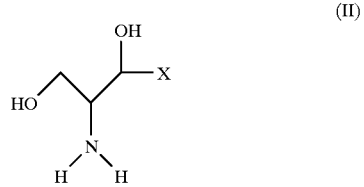

(II)

wherein

X is a branched or straight chain alkyl, alkenyl or polyalkenyl;
(b) a sphingosinephosphorylethanolamine of formula (III)

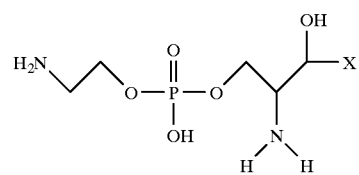

(III)

wherein

X is a branched or straight chain alkyl, alkenyl or polyalkenyl; or
(c) a ceramide mixture of formula (IV)

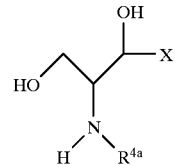

(IV)

wherein $R^{4a}$ is $C(O)R^{8a}$;

$R^{8a}$ is $(C_{13}-C_{23})$alkyl, $(C_{13}-C_{23})$alkenyl or poly $(C_{13}-C_{23})$alkenyl, all of which may be a straight or a branched chain;

X is a branched or straight chain alkyl, alkenyl or polyalkenyl; and the enantiomorphs and structural isomers thereof; and
(v) reacting a sphingosine of formula (II), a sphingosinephosphorylethanolamine of formula (III) or a ceramide mixture of formula (IV) with one or more suitable organic reactants to form a daughter sphingolipid of formula (V).

14. The process of claim 13 to produce a daughter sphingolipid of formula (V) wherein $R^5$ is a hydrogen atom, hydroxyl, mercapto, amino, monosubstituted amino, disubstituted amino, $OC(O)R^6$ or $OR^6$, or together with the carbon to which it is attached forms a keto group;

$R^6$ is $(C_1-C_6)$alkyl, $(C_2-C_6)$alkenyl, $(C_2-C_6)$alkynyl, aralkyl or heterocyclylalkyl which is cyclic, branched or straight chain, and which may be substituted by one or more conventional pharmaceutically acceptable substituents such as halo, nitro, hydroxyl and the like;

Q is a hydrogen atom, hydroxy, mercapto, $NR^1R^2$, formyl, alkanoyl, $OC(O)R^6$, $OR^6$, a phosphate or substituted phosphate, a phosphonate or substituted phosphonate, a nucleotide, a nucleoside, a polynucleotide, a polynucleoside, an amino acid, a peptide, a saccharide or a polysaccharide;

$R^1$ and $R^2$ are independently a hydrogen atom, lower alkyl, $C(O)R^7$, $C(O)OR^7$ or together with the nitrogen atom to which they are attached form a nitro group or a nitrogen atom containing heterocyclic ring of 3–7 ring members;

$R^7$ is alkyl, alkenyl, alkynyl, aralkyl or heterocyclylalkyl which is cyclic, branched or straight chain, and which may be substituted by one or more conventional pharmaceutically acceptable substituents such as halo, nitro, hydroxyl and the like;

$R^3$ and $R^4$ are independently a hydrogen atom, lower alkyl, $C(O)R^8$, $C(O)OR^8$ or together with the nitrogen atom to which they are attached form a nitro group or a nitrogen atom containing heterocyclic ring of 3–7 ring members;

$R^8$ is $(C_1-C_{23})$alkyl, $(C_2-C_{23})$alkenyl, poly$(C_4-C_{23})$ alkenyl, $(C_2-C_{23})$alkynyl, aralkyl or heterocyclylalkyl which is cyclic, branched or straight chain, and which may be substituted by one or more conventional pharmaceutically acceptable substituents such as halo, nitro, hydroxyl and the like; and the enantiomorphs and structural isomers thereof.

15. The process of claim 14 to produce a daughter sphingolipid of formula (V) wherein Q is selected from the group consisting of hydroxyl, glycyl, arginyl, lysyl, galactosyl, sulfogalactosyl, glucosyl, inositol, lactosyl, trihexosyl, phosphorylcholine, phosphorylethanolamine, GalNAc-Gal-Glc, Gal-Gal-Glc, Sia-Gal-Glc,

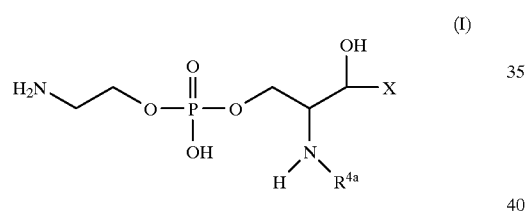

16. The process of claim 15 to produce a daughter sphingolipid of formula (V) wherein Q is glucosyl, $R^8$ is CH(OH)—(CH$_2$)$_n$CH$_3$ and n is 11–21.

17. A method comprising the treatment of a plant with an agronomically effective amount of (i) a compound of formula (I)

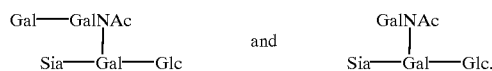

(I)

wherein $R^{4a}$ is $C(O)R^{8a}$;

$R^{8a}$ is $(C_{13}-C_{23})$alkyl, $(C_{13}-C_{23})$alkenyl or poly$(C_{13}-C_{23})$alkenyl, all of which may be a straight or a branched chain;

X is a branched or straight chain alkyl, alkenyl or polyalkenyl; and the enantiomorphs and structural isomers thereof;

(ii) a compound of formula (II)

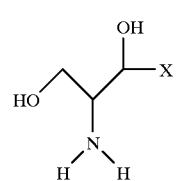

(II)

wherein

X is a branched or straight chain alkyl, alkenyl or polyalkenyl; and the enantiomorphs and structural isomers thereof;

(iii) a compound of formula (III)

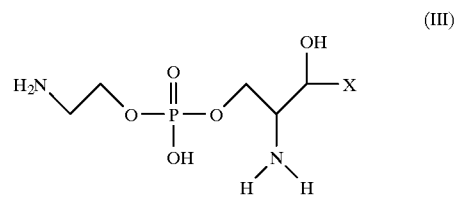

(III)

wherein

X is a branched or straight chain alkyl, alkenyl or polyalkenyl; and the enantiomorphs and structural isomers thereof; or (iv) a compound of formula (IV)

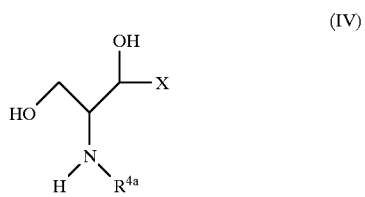

(IV)

wherein $R^{4a}$ is $C(O)R^{8a}$;

$R^{8a}$ is $(C_{13}-C_{23})$alkyl, $(C_{13}-C_{23})$alkenyl or poly$(C_{13}-C_{23})$alkenyl, all of which may be a straight or a branched chain;

X is a branched or straight chain alkyl, alkenyl or polyalkenyl; and the enantiomorphs and structural isomers thereof.

* * * * *